US006970585B1

(12) United States Patent
Dafni et al.

(10) Patent No.: US 6,970,585 B1
(45) Date of Patent: Nov. 29, 2005

(54) REAL-TIME DYNAMIC IMAGE RECONSTRUCTION (75) Inventors: Ehud Dafni, Caesarea (IL); Uri Shreter, Beachwood, OH (US); Haim Gelman, Migdal-Haemek (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/380,654

(22) PCT Filed: Feb. 12, 1998

(86) PCT No.: PCT/IL98/00074

§ 371 (c)(1),
(2), (4) Date: Apr. 13, 2001

(87) PCT Pub. No.: WO98/36690

PCT Pub. Date: Aug. 27, 1998

(30) Foreign Application Priority Data

Feb. 20, 1997 (IL) ..................................... 120277
Feb. 20, 1997 (IL) ..................................... 120278

(51) Int. Cl.$^7$ ............................................. G06K 9/00
(52) U.S. Cl. ...................... 382/131; 382/132; 600/440; 128/922
(58) Field of Search ................................ 382/131, 132, 382/128; 250/455; 128/922; 356/39; 377/10; 378/9, 15, 65; 600/425, 420, 440; 324/307; 348/588

(56) References Cited

U.S. PATENT DOCUMENTS

| | | | |
|---|---|---|---|
| 3,866,047 A | | 2/1975 | Houndsfield |
| 4,144,457 A | * | 3/1979 | Albert ............................ 378/9 |
| 4,745,479 A | * | 5/1988 | Waehner ...................... 348/588 |
| 4,817,015 A | * | 3/1989 | Insana et al. ................ 600/437 |
| 4,920,481 A | * | 4/1990 | Binkley et al. ................ 703/26 |
| 4,981,142 A | * | 1/1991 | Dachman .................... 600/562 |
| 5,291,402 A | | 3/1994 | Pfoh |
| 5,297,215 A | * | 3/1994 | Yamagishi .................. 382/131 |
| 5,315,665 A | * | 5/1994 | Ohhashi ...................... 382/131 |
| 5,412,562 A | | 5/1995 | Nambu |
| 5,485,493 A | | 1/1996 | Heuscher et al. |
| 5,524,130 A | | 6/1996 | Ohhashi |
| 5,546,439 A | | 8/1996 | Hsieh |
| 5,585,724 A | * | 12/1996 | Morich et al. .............. 324/318 |
| 5,647,360 A | * | 7/1997 | Bani-Hashemi et al. .... 600/425 |
| 5,647,361 A | * | 7/1997 | Damadian .................... 600/411 |
| 5,751,852 A | * | 5/1998 | Marimont et al. .......... 382/180 |
| 5,754,623 A | * | 5/1998 | Seki ............................. 378/65 |
| 5,821,751 A | * | 10/1998 | Wendt et al. ................ 324/307 |
| 5,825,842 A | * | 10/1998 | Taguchi ........................ 378/15 |
| 5,841,830 A | * | 11/1998 | Barni et al. .................... 378/15 |
| 5,881,124 A | * | 3/1999 | Giger et al. .................... 378/8 |
| 5,909,477 A | * | 6/1999 | Crawford et al. .............. 378/4 |

(Continued)

FOREIGN PATENT DOCUMENTS

| | | |
|---|---|---|
| EP | 0 662 305 A | 7/1995 |
| FR | 2 679 435 A | 1/1993 |
| WO | WO 98/36691 | 8/1998 |

Primary Examiner—Bhavesh M. Mehta
Assistant Examiner—Barry Choobin (57) ABSTRACT A method for modifying a planar image slice in a CT scanner having a predetermined reconstruction angle, comprising: reconstructing an image of the slice using initial X-ray attenuation data acquired along an initial scan path sector; acquiring additional X-ray attenuation data along an additional scan path sector in a vicinity of the axial position of the slice, the sector having an angular extent substantially less than the reconstruction angle; and modifying the image, to provide a modified image of the slice, responsible to the additional attenuation data.

26 Claims, 4 Drawing Sheets

U.S. PATENT DOCUMENTS

| | | | |
|---|---|---|---|
| 5,960,102 A | * | 9/1999 | Van Eeuwijk et al. ...... 382/128 |
| 5,966,422 A | * | 10/1999 | Dafni et al. ................... 378/9 |
| 5,995,581 A | * | 11/1999 | Ozaki .......................... 378/20 |
| 6,072,851 A | * | 6/2000 | Sivers ......................... 378/15 |
| 6,219,441 B1 | * | 4/2001 | Hu ............................. 382/131 |
| 6,370,218 B1 | * | 4/2002 | Toth et al. .................... 378/19 |
| 6,573,714 B1 | * | 6/2003 | Hu et al. ..................... 324/300 |
| 6,597,936 B1 | * | 7/2003 | Liu et al. .................... 600/420 |
| 6,768,782 B1 | * | 7/2004 | Hsieh et al. ................... 378/8 |
| 2002/0138019 A1 | * | 9/2002 | Wexler et al. .............. 600/547 |

* cited by examiner

REAL-TIME DYNAMIC IMAGE RECONSTRUCTION

RELATED APPLICATION

This application is a US National filing of PCT Application PCT/IL98/00074, filed Feb. 12, 1998.

FIELD OF THE INVENTION

The present invention relates generally to computerized tomographic (CT) imaging, and specifically to CT imaging of dynamic physiological processes and interventional procedures.

BACKGROUND OF THE INVENTION

CT scanners are well known in the art. Generally, such scanners comprise an X-ray tube, mounted on an annular gantry, so as to revolve about a subject being imaged. The subject lies on a bed, which is translated through the gantry. The axis of translation of the bed (conventionally the Z-axis) is generally parallel to the long axis of the subject's body, which is typically perpendicular to the plane of revolution of the tube.

An array of X-ray detectors on the opposite side of the subject from the X-ray tube receive radiation transmitted through the subject. The detectors generate signals proportional to the attenuated X-ray flux incident thereon, corresponding to a series of circumferentially-disposed angular "views" through the subject. These signals are pre-processed to produce attenuation data, which are used in reconstructing a three-dimensional image of the subject. In "third-generation" scanners, the array of detectors is mounted on the gantry so as to revolve along with the X-ray tube, whereas in "fourth-generation" scanners, the detectors are arrayed in a ring, which is generally stationary.

CT scanners generally operate in axial or helical scan modes. In axial modes, the gantry and the bed move in alternation, i.e., the bed is held stationary at a given axial position while the gantry revolves about the subject. After a desired number of full or partial revolutions, the bed is advanced to the next, generally adjacent, axial position, and the gantry revolutions are repeated, thus continuing until all or a selected portion of the subject's body is scanned and corresponding image slices are reconstructed. In helical modes, the gantry revolves and the bed advances simultaneously, so that the X-ray tube describes a generally helical path relative to the body.

In a helical-mode scanner, in order to reconstruct a planar cross-sectional image slice of the subject at a desired axial position, based on the helical-scan views, effective attenuation values for each of a plurality of points around a circumference of such a planar slice are derived by interpolation between data received in the original helical-path views. For each of the plurality of points, the respective effective attenuation values correspond to the approximate attenuation along rays within the planar slice that pass through the point. For 360° reconstruction, as is known in the art, the plurality of points are distributed around the entire circumference of the slice, whereas for 180° reconstruction, also known in the art, the points are distributed on a half-circumference. (For convenience in the following discussion, we will refer to the total angular extent of all the views that are collectively used in the reconstruction of a complete planar slice as the "reconstruction angle," typically 360° or 180°.) The interpolated data are filtered and back-projected to produce the cross-sectional image.

Cross-sectional images thus produced by CT scanners generally lag behind the acquisition of the attenuation data by several seconds at the least. This lag stems from several factors, including (1) the necessity of receiving data from views over the entire reconstruction angle (or more, in the case of helical scanners) before reconstructing the image; and (2) the time needed to complete the intensive computations involved in back-projecting an entire image slice. The lag is particularly disadvantageous when CT imaging is used to track the progress of a physiological process, such as the flow of a contrast material. Similarly, when the CT scanner is used to guide a surgical procedure, such as a biopsy, the surgeon receives visual feedback regarding his progress in the procedure with a delay of more than one scan period.

Multi-slice axial and helical-path scanners are known in the art. For example, U.S. Pat. No. 5,485,493, which is incorporated herein by reference, describes a multiple-detector-ring spiral scanner with relatively adjustable helical paths, in which two adjacent, parallel slices are acquired along two parallel paths simultaneously or sequentially. Data corresponding to planar slices are derived by interpolating between data acquired along the two helical paths.

U.S. Pat. No. 5,524,130, the disclosure of which is incorporated herein by reference describes a number of methods for utilizing a single detector ring scanner to provide successive axially spaced slices with reduced time between reconstruction of the slices. Some of these methods appear to utilize partial scan data from one scan to replace data from a second scan for reducing the reconstruction time.

SUMMARY OF THE INVENTION

It is an object of the present invention to provide a method for rapid image reconstruction based on axial or helical-scan CT data.

In one aspect of the present invention, the CT data comprise multiple-slice CT data, acquired using a multi-row detector array.

In another aspect of the present invention, helical-scan data are used to reconstruct planar corrected image slices, which are displayed sequentially as the scan proceeds.

It is a further object of the present invention to provide a method for near-real-time CT imaging of physiological processes and interventional treatments.

In preferred embodiments of the present invention, a CT scanner comprises an X-ray tube, mounted to revolve on an annular gantry about a bed on which a subject lies, and a detector array. The bed is advanced through the gantry along a translation axis that is generally parallel to the long axis of the subject's body. The X-ray tube thus irradiates the subject from multiple positions, or "views," along this trajectory. The detector array comprises at least one and preferably two or more parallel rows of X-ray detector elements in a multi-row detector array, each row having a long axis disposed in a generally circumferential direction with respect to the long axis of the subject's body.

The detector elements receive radiation that has passed through the subject's body at each of the views and generate signals responsive to attenuation of the X-rays. These signals are preprocessed, as is known in the art, to generate effective attenuation values, which are associated with planar slices through the body that are generally perpendicular to the translation axis. Optionally, the attenuation values are re-binned, as is known in the art, to arrange the values in a format corresponding to an array of parallel beams through the body. The attenuation values are filtered and back-projected to calculated CT values, which are used to reconstruct cross-sectional CT images and then to update the images substantially in real time.

In some preferred embodiments of the present invention, the CT scanner is a multiple slice helical-path scanner as described in an Israel patent application entitled "On-Line Image Reconstruction in Helical CT Scanners," filed on Feb. 20, 1997 and assigned application number 120277 and a PCT application having the same title filed on even date with the present application, whose disclosures are incorporated herein by reference. In these embodiments, effective attenuation values are calculated for each of a plurality of points on a periphery of each planar slice by weighted interpolation between first and second measured attenuation values, taken from respective first and second line images within a single view. The first and second line images are derived respectively from data received simultaneously from first and second rows of detector elements. Thus, a complete cross-sectional CT image is reconstructed within a time window corresponding to a single, initial revolutionary scan of the tube over the reconstruction angle, typically 180° or 360°.

In preferred embodiments of the present invention, an initial planar image slice is reconstructed at a selected axial position as described above, using data from a 360° (or 180°) scan in a vicinity of the position, along either an axial or a helical scan path. The initial image is then updated and modified continually by incorporation of additional attenuation data acquired from angular views further along the scan path, as the tube continues to revolve.

Preferably, the planar image is displayed, for example on a CRT display screen, as is known in the art, and the display is updated continually as the image is updated. Additionally or alternatively, as the image is updated, it is recorded in digital or analog format for subsequent playback.

Further preferably, the additional data are processed so as to back-project effective attenuation values derived from the additional data and thus to produce an image data matrix. This matrix is added to the planar slice image, while a similar matrix, back-projected from values derived from the data acquired from the preceding scan, is subtracted.

Alternatively, processing the additional data may include adding the additional data and subtracting corresponding data acquired in the preceding scan, or taking the difference of respective effective attenuation values derived from the additional and the preceding data. The resultant difference is back-projected to produce an image data matrix, which is added to the planar slice image.

In some preferred embodiments of the present invention, a region of interest (ROI) is designated within a selected planar image slice, and the image in this ROI is updated, using methods described above, at a higher update rate than the remainder of the slice image. Limiting the image updating operation to the ROI allows the ROI image to be reconstructed more rapidly than the entire slice could be updated. When changes take place within the ROI, they are thus displayed in the reconstructed image with a shorter time lag than could be achieved if the entire slice were updated.

Preferably, the full planar image slice is reconstructed intermittently, and the ROI image is registered with the full slice image.

In some preferred embodiments of this type, the ROI is selected to include an object of interest, for example, a biopsy needle. The position of the object in the image is tracked, preferably using means and methods of automated image analysis known in the art, and the boundaries of the ROI are varied as appropriate to keep the object within the ROI.

In some preferred embodiments of the invention, this tracking of position takes place within a slice, in other preferred embodiments of the invention, where multiple slices are reconstructed and optionally displayed, tracking takes place intra-slice and slices are presented and/or reconstructed such that the slice which contains the needle tip is in or near the center of the group of slices which are reconstructed. Where only a single slice is displayed, the displayed slice is changed such that the slice which contains the needle tip is presented. Optionally, a new slice is reconstructed in which the needle tip is substantially axially centered.

It will be appreciated that the principles of the present invention are equally applicable to third- and fourth-generation CT scanners, and to various image reconstruction methods, including 180°, 360°, fan beam and parallel beam reconstruction, as are known in the art. Furthermore, although some preferred embodiments of the present invention are described with reference to multi-slice, helical-path scanners, the principles of the present invention are similarly applicable to both single-slice and multi-slice axial-scan CT systems.

Moreover, although in the preferred embodiments described herein, the Z-axis, along which the bed advances, is generally perpendicular to the plane of revolution of the tube, the principles of the present invention may similarly be applied to CT image reconstruction using angled helical scan paths, as described in a PCT patent application PCT/IL97/00069, filed on Feb. 20, 1997, entitled "Helical Scanner with Variably Oriented Scan Axis," which is assigned to the assignee of the present invention, and whose disclosure is incorporated herein by reference. This application designates the US.

There is therefore provided, in accordance with a preferred embodiment of the present invention, a method for modifying a planar image slice in a CT scanner having a predetermined reconstruction angle, comprising:

reconstructing an image of the slice using initial X-ray attenuation data acquired along an initial scan path sector;

acquiring additional X-ray attenuation data along an additional scan path sector in a vicinity of the axial position of the slice, the sector having an angular extent substantially less than the reconstruction angle; and modifying the image, to provide a modified image of the slice, responsive to the additional attenuation data.

Preferably the method includes defining a region of interest within the image slice, wherein modifying the image comprises modifying only a portion of the image corresponding to the region of interest. Preferably, defining the region of interest comprises identifying an object of interest and altering the region of interest in response to movement of the object. Preferably, altering the region of interest in response to movement of the object comprises determining a characteristic of the X-ray attenuation data indicative of the position of the object, and shifting the region of interest in response to a change is the characteristic. Preferably, determining the characteristic of the X-ray attenuation data comprises finding a maximum value of the data within a data window corresponding to the region of interest. Preferably, finding the maximum value of the data comprises pre-processing the data and finding a maximum value of the pre-processed data.

In a preferred embodiment of the invention, acquiring the data along the initial and additional scan path sectors comprises acquiring multi-slice data along the sectors of the scan path. Preferably, acquiring data along the sectors of the scan path comprises acquiring the data along sectors of a helical scan path. Alternatively, acquiring the data along the scan path sectors comprises acquiring the data along sectors of a generally circular scan path substantially within a plane at the axial position of the slice.

In a preferred embodiment of the invention, modifying the image responsive to the additional attenuation data comprises processing the additional attenuation data and the initial attenuation data to produce an image data matrix and adding the matrix to the image.

Preferably processing the attenuation data to produce the image data matrix comprises:
 back-projecting attenuation values calculated from the additional data, to determine a first preliminary matrix;
 back-projecting attenuation values calculated from the initial data that were acquired in a portion of the initial scan path sector corresponding to the additional scan path sector, to determine a second preliminary matrix; and
 subtracting the second preliminary matrix from the first preliminary matrix to produce the image data matrix.

Alternatively, processing the attenuation data to produce the image data matrix comprises:
 calculating initial attenuation values from the initial data that were acquired in a portion of the initial scan path sector corresponding to the additional scan path sector;
 calculating additional attenuation values from the additional data;
 subtracting the initial attenuation values from the additional attenuation values to determine difference values; and
 back-projecting the difference data to produce the image data matrix.

There is further provided, in accordance with a preferred embodiment of the invention, a method for producing a CT image of a region of interest within the body of a subject, comprising:
 reconstructing a CT image of a slice of the body;
 defining the region of interest; and
 updating the CT image only in the region of interest, wherein the image of the region of interest encompasses only a portion of the CT image of the slice.

Preferably, the method comprises superimposing the CT image of the region of interest on another CT image encompassing a substantially greater portion of the cross-sectional area. Preferably, the updated image of the region of interest is produced utilizing one of the above defined methods.

In a preferred embodiment of the invention, the region of interest is determined based on an expectation of change in the CT image in the region of image.

Additionally or alternatively, the method includes identifying an object of interest and wherein defining the region of interest comprises defining the region of interest in response to a determination of the position of the object of interest. Preferably, the method comprises altering the region of interest being reconstructed in response to movement of the object.

In a preferred embodiment of the invention, altering the region of interest in response to movement of the object comprises determining a characteristic of the X-ray attenuation data indicative of the position of the object, and shifting the region of interest being reconstructed in response to a change in the characteristic. Preferably, determining the characteristic of the X-ray attenuation data comprises finding an extremum value of the data within a data window corresponding to the region of interest. Preferably, finding the extremum value of the data comprises preprocessing the data and finding a maximum value of the pre-processed data.

In a preferred embodiment of the invention, the CT image is a multi-slice image and wherein the position of the slices are determined based on a determination of the position of the object with respect to the slices.

There is further provided, in accordance with a preferred embodiment of the invention, a method of determining an optimal position for multiple CT slices, comprising:
 reconstructing the multiple slices based on a first set of data;
 determining the position of an object in the slices;
 then reconstructing the slices based on the determined position.

In a preferred embodiment of the invention, the object is a biopsy needle.

There is further provided, in accordance with a preferred embodiment of the invention, an imaging method for the determination of the position of a biopsy needle comprising:
 reconstructing a CT image from a plurality of views;
 determining the position of the biopsy needle in the image; and
 determining a region of interest based on the determined position of the biopsy needle.

In a preferred embodiment of the invention, the method includes periodically updating the image only in the region of interest.

There is further provided, in accordance with a preferred embodiment of the invention, an imaging method for imaging a region in a region of interest in which changes are expected comprising:
 reconstructing a CT image from a plurality of views; and
 periodically modifying the image only in the region of interest.

In a preferred embodiment of the invention, the image is periodically modified utilizing one of the above defined methods.

The present invention will be more fully understood from the following detailed description of the preferred embodiments thereof, taken together with the drawings in which:

DETAILED DESCRIPTION OF PREFERRED EMBODIMENTS

Figure 1:
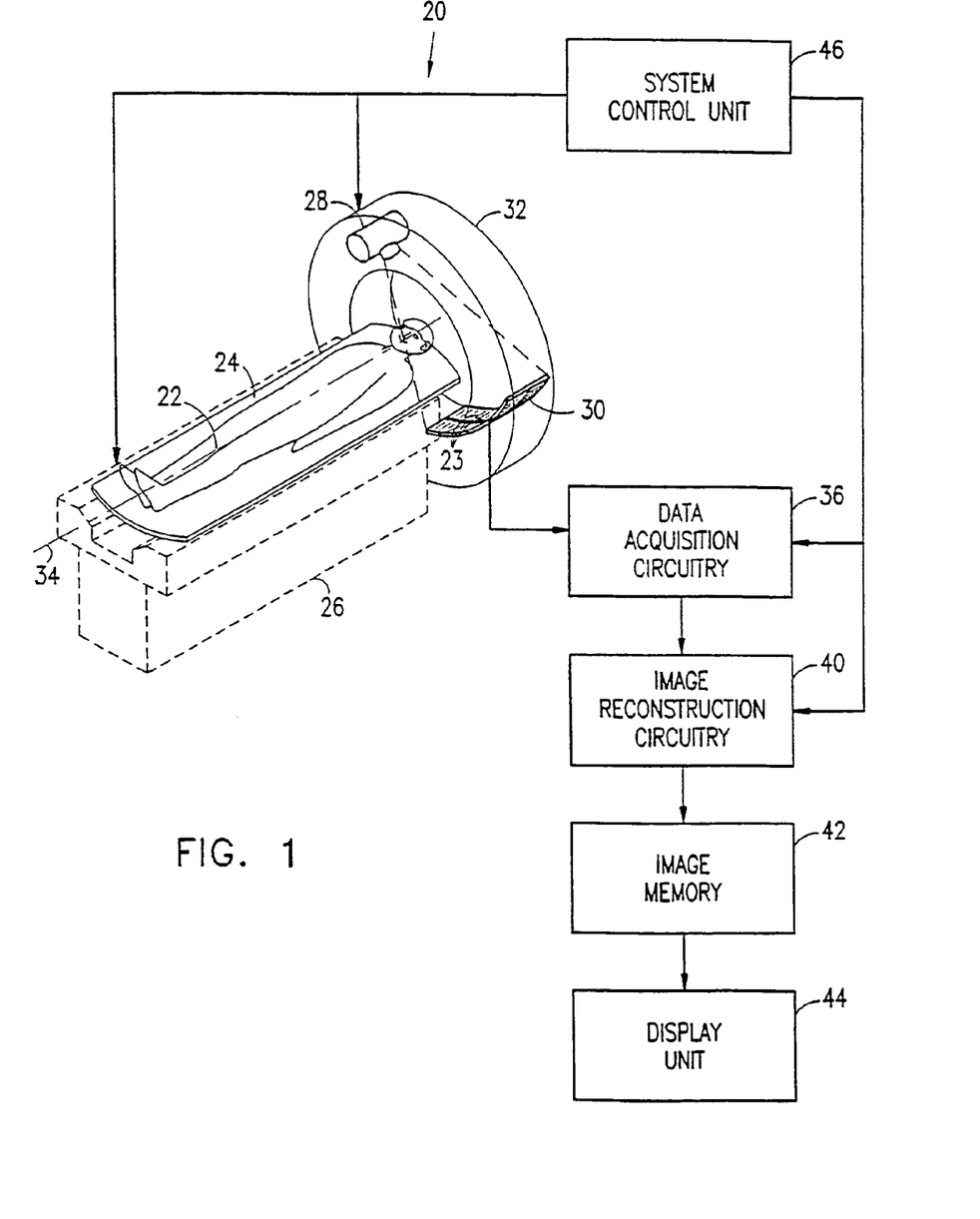
FIG. 1 is a schematic illustration of a CT scanner, operative in accordance with a preferred embodiment of the present invention.

Reference is now made to FIG. 1, which shows a CT scanner 20, operative in accordance with a preferred embodiment of the present invention. Scanner 20 comprises a bed 24, supported by a base 26, on which bed a subject 22 lies while his body is being imaged by the scanner. Scanner 20 further comprises an X-ray tube 28, which irradiates subject 22, and a detector array 30, which receives X-rays from tube 28 and generates signals responsive to the attenuation of the X-rays in passing through the subject's body. Preferably, array 30 comprises multiple, parallel rows of X-ray detector elements 23. Alternatively, array 30 may comprise only a single row of detector elements.

Tube 28 and array 30 are mounted on an annular gantry 32, so as to revolve about subject 22. Bed 24 is advanced through gantry 32 along an axis 34, taken to be the Z-axis of a scanning coordinate system. Z-axis 34 is generally parallel to the long axis of the subject's body. Scanner 20 preferably operates in an axial mode, wherein bed 24 is held stationary while tube 28 and array 30 revolve there about. However, in some aspects of the invention, scanner 20 may alternatively operate in a helical mode, wherein tube 28 and array 30 revolve simultaneously with the advance of bed 24 through gantry 32.

Scanner 20 as pictured in FIG. 1 is of a type known in the art as a third-generation CT-scanner, characterized in that both tube 28 and detector array 30 revolve about subject 22. It will be appreciated, however, that the principles of the present invention and the methods of image reconstruction to be described below are equally applicable to other types of CT scanners, in particular fourth-generation CT scanners, in which the detectors form a substantially stationary ring around subject 22.

At each of a plurality of selected locations of tube 28 along its scan path, data acquisition circuitry 36 acquires a "view," i.e., the circuitry receives signals from each element 23 of array 30 responsive to X-ray attenuation along a ray from tube 28 to the element. Each such view comprises one or more parallel line images, each line image corresponding to one of the one or more rows of array 30.

For each view, data acquisition circuitry 36 performs signal normalization and logarithm operations, as are known in the art, to derive X-ray attenuation data corresponding to each of elements 23. Image reconstruction circuitry 40 receives these data and derives effective attenuation values at a plurality of points on a periphery of a planar image slice, at a selected position along Z-axis 34. These effective values are filtered and back-projected, using methods known in the art, to produce a planar image slice at the selected position. A plurality of these planar image slices are typically produced, so as to reconstruct a three-dimensional CT image set of the body of subject 22. Preferably, these image slices are stored in image memory 42 and displayed by display unit 44, and they may be otherwise printed and/or processed as is known in the art.

In some preferred embodiments of the present invention, in which CT scanner 20 operates in an axial scan mode, an image slice is reconstructed at a given axial position of bed 24 after views have been acquired over an angular scan extent that is generally equal to the reconstruction angle, for example, 180°, at the axial position, as is known in the art. Thereafter, tube 28 continues to revolve about subject 22 at this position, and this original image is modified and updated, as will be described below, by incorporating attenuation data acquired in additional angular views, for as long as bed 24 remains at this axial position.

In other preferred embodiments of the present invention, in which scanner 20 operates in a helical scan mode, an image slice at a given axial position is similarly reconstructed, as described in a PCT patent application entitled "On-line Image Reconstruction in Helical CT Scanners," filed on even date, which is referenced above and which is incorporated herein by reference. The initial image is first reconstructed using views acquired over a portion of the helical scan path having an angular extent generally equal to the reconstruction angle, for example, 180°, in a vicinity of the axial position. Thereafter, this initial image is modified and updated, as will be described below, by incorporating attenuation data acquired at additional view angles along the helical path. This modification and updating can continue for as long as tube 28 and array 30 dwell close enough to the axial position of the slice so that the slice remains within the detection area of at least one of the rows of the array. Preferably, the helical scan path has a pitch that is substantially less than the width of array 30, so that the dwell time of tube 28 and array 30 at a given position is equal to at least the period of one complete revolution about subject 22.

Figure 2:
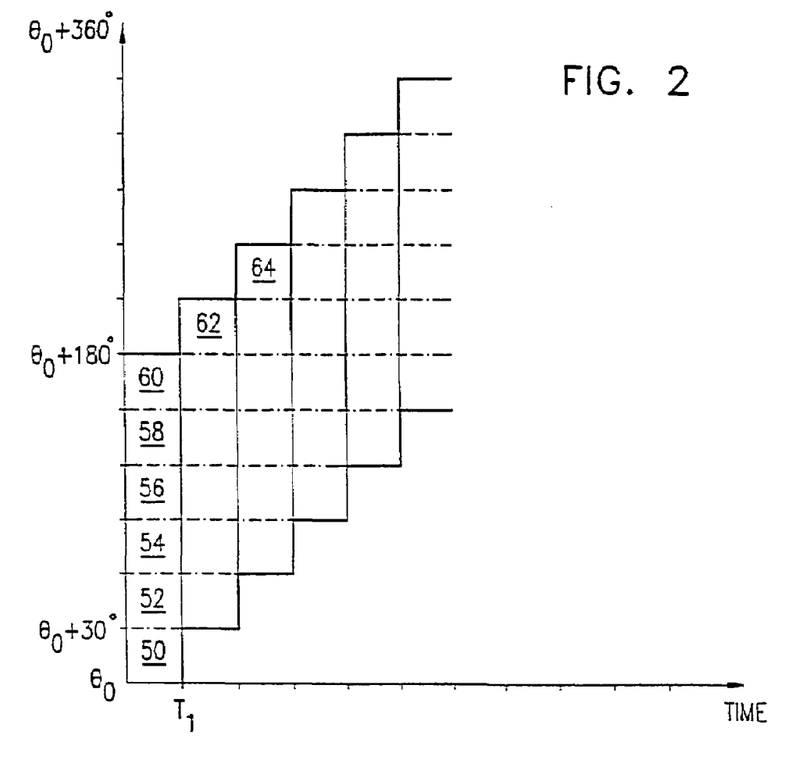
FIG. 2 is a graph that schematically illustrates an aspect of the operation of the scanner of FIG. 1, in accordance with a preferred embodiment of the present invention.

FIG. 2 is a graph that schematically illustrates ranges of view angles θ over which attenuation data are acquired, as a function of time, for the purpose of reconstructing and updating a planar slice image at a given axial position Z, in accordance with preferred embodiments of the present invention. Initially, views of subject 22 are acquired as tube 28 scans through a 180° angular range from $\theta_o$ to $\theta_o+180°$, finishing at a time $T_1$. This range is divided into six 30° sectors, labeled 50, 52, 54, 56, 58 and 60 in FIG. 2. Generally, each of the sectors includes a plurality of views. The attenuation data acquired in each of these sectors are interpolated and back-projected to produce a partial data matrix, and the six data matrices thus produced are combined to reconstruct the planar slice image, using 180° reconstruction.

The tube is then scanned through the next 30° sector, labeled 62, and attenuation data are acquired from the same views as in sector 50 (although now seen from the opposite side of the body of subject 22). The data acquired in sector 62 are interpolated, filtered and back-projected, as described above, to produce a new partial data matrix, which is added into the planar slice image, and the matrix corresponding to sector 50 is subtracted out. In this way, changes in the body of subject 22 occurring in the area of the slice may be observed in the image. Alternatively, the partial data matrix corresponding to sector 62 may be averaged in with the matrix corresponding to sector 50, so as to smoothly alter and improve the quality of the image.

As the scan proceeds through the next 30°, a partial data matrix is produced corresponding to the next sector, labeled 64, replacing the matrix of sector 52, and so forth. The planar slice image is thus updated continually, continuing indefinitely in the case of axial scanning, or for the dwell time of the scan at position Z for helical scanning.

Alternatively, in accordance with another preferred embodiment of the present invention, the planar slice image is initially reconstructed, based on the attenuation data from sectors 50 through 60, and is then updated for every sector by adding a corresponding difference matrix to the image. The first such difference matrix is produced by (1) preprocessing and interpolating attenuation data acquired in sector 62 to derive effective attenuation values; (2) subtracting therefrom corresponding attenuation values derived from the attenuation data acquired previously in sector 50, and (3) filtering and back-projecting the difference of the sector 62 and sector 50 values to obtain the difference matrix elements. This procedure is repeated for sector 64, and so forth. In this preferred embodiment, it is not necessary to produce and save the partial data matrices for the 30° scan sectors; rather, the pre-processed attenuation data are stored and used in the updating calculation.

It will be appreciated that 30° scan sectors are used in the above preferred embodiments and in FIG. 2 for illustrative purposes only, and any other suitable sector size may be used. In particular, each sector may correspond to a single view, with each such sector having an extent equal to the angular increment between one view and the next, for example, 1°. The slice image can thus be updated every time a new view is acquired, preferably using a pipeline processing architecture.

It will further be appreciated that the above method is described with reference to 180° reconstruction by way of example only, and it may easily be adapted for use with 360° reconstruction, as well.

By using the above method, with sufficiently small scan sectors, changes in the body of subject 22, such as the flow of a contrast medium or insertion of a biopsy instrument, will appear as quasi-continuous changes in the image displayed by display unit 44. The image will still have a certain lag behind the actual changes, however, due to the pipeline processing delay and to the fact that only one or a few views are changed each time the image is updated. The changing image may also be stored digitally or in analog form, on videotape, for example, for later replay and review.

Figure 3:
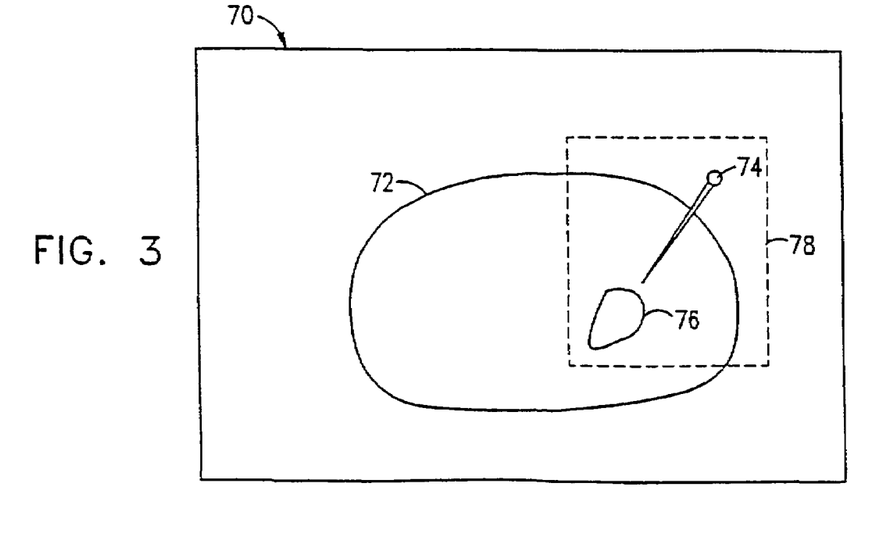
FIG. 3 is a schematic illustration of a CT image showing an interventional procedure performed on the body of a subject, in accordance with a preferred embodiment of the present invention.

FIG. 3 is a schematic illustration of a CT slice image 70, acquired by CT scanner 20 in accordance with a preferred embodiment of the present invention. Image 70 shows a cross-sectional slice 72 through the body of subject 22, while a biopsy needle 74 is in the course of being inserted into an organ 76 of the subject. A region of interest (ROI) 78 is defined, either by a user of scanner 20 or automatically by software running in the scanner, to include needle 74 and organ 76. As illustrated in the figure, the area of ROI 78 is roughly one fourth the area of image 70, but a larger or smaller ROI may be defined as needed.

Because ROI 78 is substantially smaller than image 70, the portion of the image within the ROI can be separately updated by image reconstruction circuitry 40 at a higher update rate, and/or with a shorter image lag (as described above), than would be possible for updating the entire image. Therefore, in some preferred embodiments of the present invention, methods of updating the image sector-by-sector, as were described above, are applied to produce a quasi-continuous, time-varying image only of the ROI. This ROI image is used, for example, to track the insertion of needle 74 into organ 76.

In one preferred embodiment of the invention, all of the data in the views is preprocessed and filtered and only the data used for the ROI is projected. In a second preferred embodiment of the invention, only data needed for the ROI (including the data outside the ROI needed for determining the values within the ROI) is processed and interpolated data is used for the missing parts of the views outside the ROI. In a third preferred embodiment of the invention, assuming that the patient is not moving, is to use the view data outside the ROI from the previous rotation.

Preferably, the time-varying image of ROI 78 is registered with and superimposed on the relatively static image 70.

Alternatively, within the area of image 70, the ROI image may be reconstructed and displayed by itself, while the remainder of the image slice is not reconstructed or displayed.

Further preferably, the position of needle 74 is tracked by CT scanner 20, and the position of ROI 78 is intermittently adjusted in response to changes in the position of needle 74. The position of needle 74 may be tracked using image analysis and tracking software known in the art. Preferably, however, movement of the top of needle 74 is tracked using pre-processed attenuation data acquired from array 30, before performing image reconstruction for the sector. In this way, the time lag between movement of the needle and adjustment of the position of ROI 78 in response thereto is reduced, and the ROI is optimally positioned to include needle 74 and other features of interest, prior to reconstruction.

Preferably, in order to track the top of needle 74 using the pre-processed attenuation data, the ROI image is first reconstructed, and a small sub-region centered on the needle top is defined within this image. The CT values in the ROI are reprojected back to the preprocessed data set, so as to define a data window corresponding to the ROI, and the sub-region values are similarly reprojected to define a corresponding sub-window. Within this sub-window, the maximum value of the data is found, and the window is shifted so that the location of the maximum value is at the center of the window. Note that this "maximum" point corresponds to a minimum in the raw (attenuation) data and a maximum in the preprocessed data. Finding of this maximum is aided by subtracting the data for each view from data acquired previously for the view. The maximum is then found from the difference data. If the patient moves (i.e., if the residuals after subtraction are high) the two sets of data are registered prior to subtraction.

Subsequently, for each new view acquired by circuitry 36, or alternatively, once in every several views, the attenuation data are pre-processed, a new maximum value and the location of the new maximum within the window are found. This new maximum value is compared to the preceding maximum value. The location of the new maximum is compared with the previous location of the maximum and with the direction and velocity of movement of the location of the maximum over the preceding views. If the new maximum value is within a predetermined threshold of the preceding value, and if the location of the new maximum is within predetermined bounds of the preceding location, based on the direction and velocity of movement, then the window is shifted so that the location of the new maximum value is at the center of the window.

If the difference of the maximum values exceeds the threshold, or if the location of the maximum is outside the predetermined bounds, however, it is assumed that the new maximum value is due to a data artifact. In this case, the window is maintained at its previous position until the maximum value returns to a value within the threshold, or until the ROI image is again reconstructed, and the actual position of needle 74 in the image may be identified.

Alternatively, "raw" attenuation data received from array 30, before preprocessing, may be similarly used in tracking needle 74 using an algorithm similar to that described above. Further alternatively, the needle may be tracked using data that has been preprocessed and filtered, before back-projection to find the CT values.

It will be appreciated that the method described here of finding and tracking the movement of a feature, such as the maximum attenuation value, in image 70 may also be used to detect and correct motion artifacts in the image. For example, a local maximum value of the pre-processed attenuation data, corresponding to an anatomical characteristic of interest, may be identified and tracked. If the location of the maximum value shifts, the CT image may be corrected, using image processing algorithms known in the art, to compensate for the shift.

Figure 4:
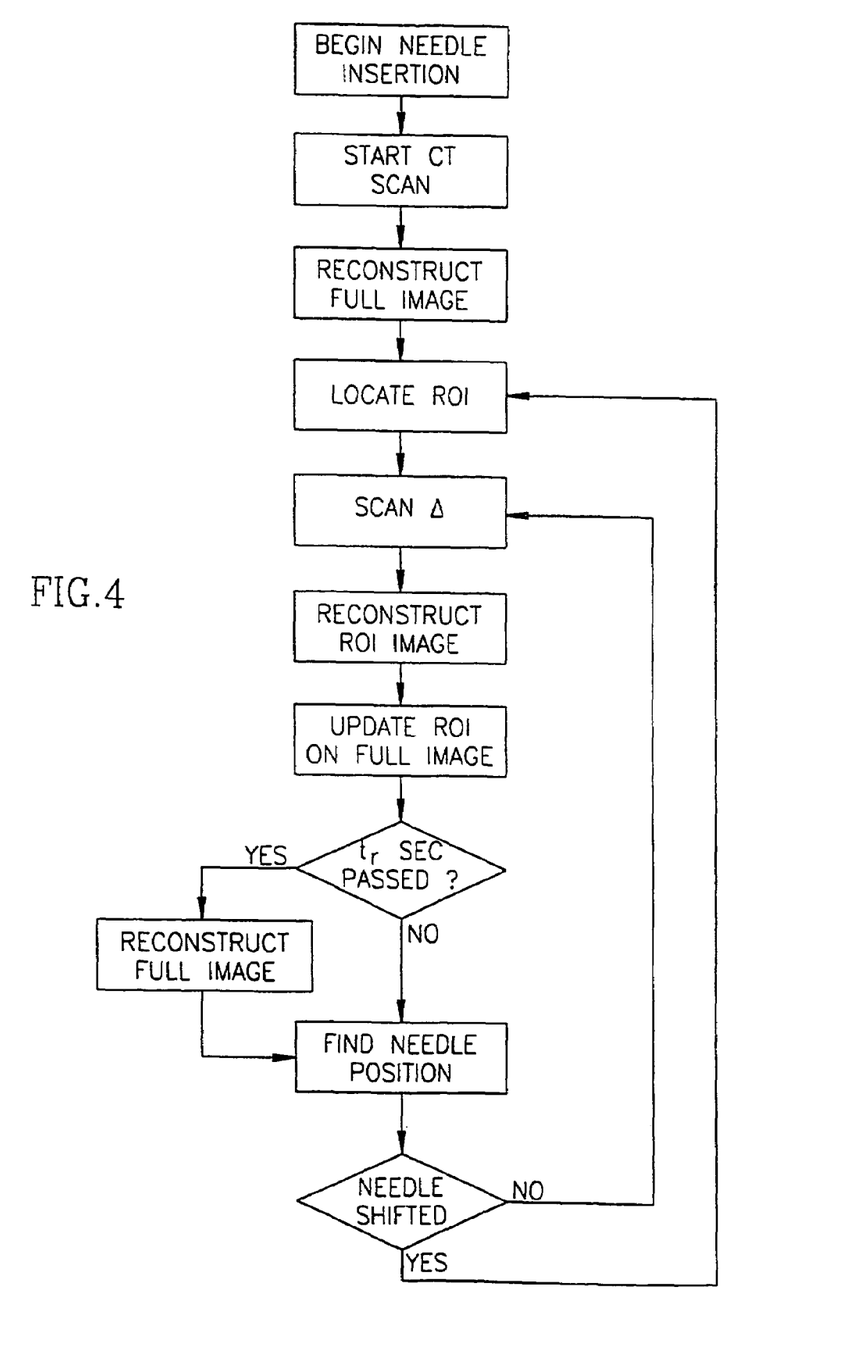
FIG. 4 is a flow chart schematically illustrating a method used in performing the procedure of FIG. 3, in accordance with a preferred embodiment of the present invention.

FIG. 4 is a flow chart schematically illustrating such a method of ROI image reconstruction, in accordance with a preferred embodiment of the present invention. Needle 74 is inserted through the skin of subject 22, at an appropriate location in proximity to organ 76. CT scanner 20 begins to operate, and after tube 28 has scanned at least 180°, a full image 70 is initially reconstructed. The boundaries of ROI 78 are then located relative to image 70, either automatically, as described above, or under the control of an operator of the scanner.

Tube 28 continues to scan through the next sector, having an angular extent Δ, for example, Δ=30° as illustrated in FIG. 2 and described with reference thereto, or Δ=1°, as described above, and attenuation data are acquired with respect to the views in this sector. These data are then used to update only the portion of the image within ROI 78, while the remainder of image 70 is left unchanged. The reconstructed ROI section of image 70 is updated on display unit 44. The position of needle 74 in the ROI is identified, and if the needle has substantially shifted relative to its earlier known position, the boundaries of ROI 78 are altered accordingly. Tube 28 scans the subsequent sectors, and the ROI image is updated, preferably at a rate of 8–10 images per second.

After a suitable period of time $t_r$, for example 1.5 seconds, the full image 70 is again reconstructed, using the most recently acquired 180° scan data. The position of needle 74 in this image is similarly identified, and if the needle has substantially shifted relative to its earlier known position, the boundaries of ROI 78 are altered accordingly. Scanning and image reconstruction for the ROI portion of the image then continue, as described above.

It will be appreciated that the principles of the present invention with regard to quasi-continuous ROI image updating may be applied to both axial-scan and helical-scan CT systems. It will further be apparent to those skilled in the art that the principles of the present invention may be applied to CT scanners of various types, including multi-slice scanners, which simultaneously produce multiple image slices, and oblique scanners, which produce image slices along planes at oblique angles relative to the long axis of the subject's body.

Furthermore, it should be understood that, while the invention has been described above with a complete reconstruction being performed, for each segment of acquired data, for bolus tracking and only an ROI is constructed for biopsy needle tracking, in other preferred embodiments of the invention only ROIs are reconstructed for bolus tracking and the entire image is reconstructed for biopsy needle tracking, for each segment of acquired data.

In a preferred embodiment of the invention, preferably using multi-slice scanners (either helical scan or more preferably stationary bed), having multiple rows of detectors, a plurality of slices are acquired simultaneously and preferably simultaneously reconstructed. Such slices may be reconstructed utilizing interpolation between the multiple slices or helical sets of data. As indicated above, the same slices are generated continuously or intermittently using the above described system of partial replacement of data for updating of images.

Figure 5A:
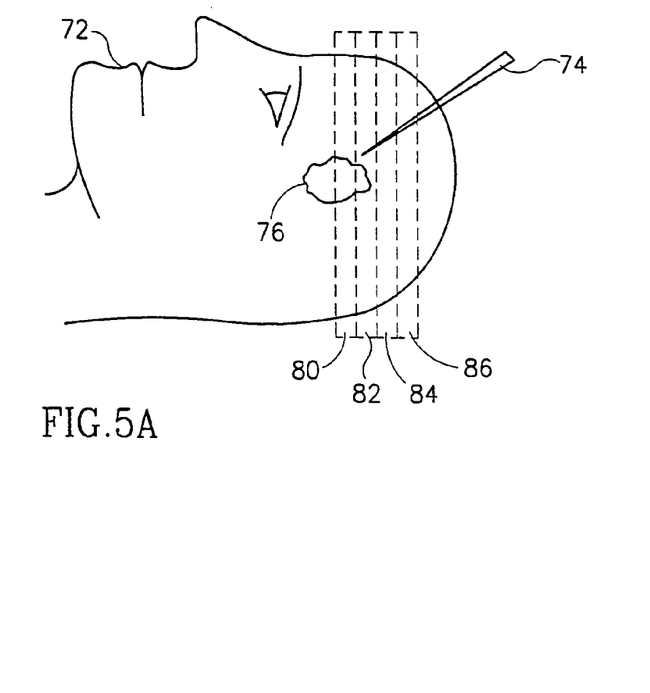
FIGS. 5A and 5B are schematic illustrations of a CT imaging of an interventional procedure performed on the body of a subject, in accordance with a preferred embodiment of the present invention utilizing a multi-slice system.
Figure 5B:
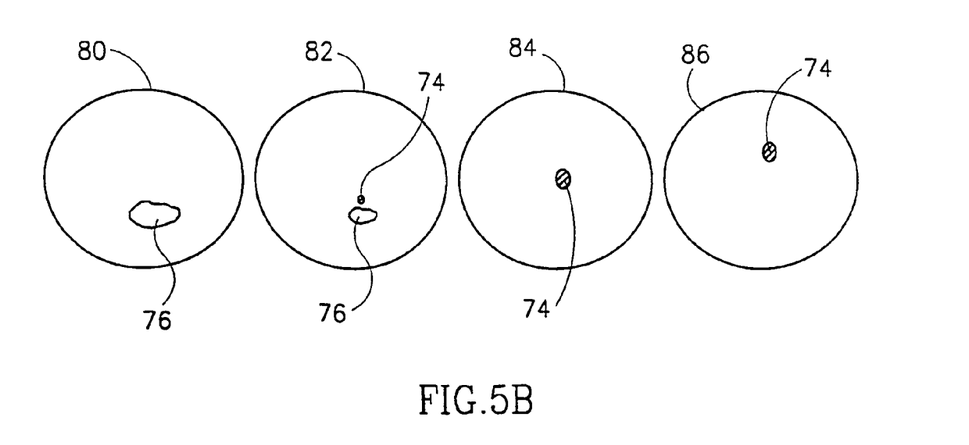

FIGS. 5A and 5B illustrate this method. FIG. 5A shows a view of the same insertion of a biopsy needle as shown in FIG. 3. However, while FIG. 3 shows a single slice, FIG. 5A is a view taken at 90 degrees to that of FIG. 3 showing the outline of four slices 80, 82, 84 and 86 superimposed (as dotted lines) on the schematic body of the patient. FIG. 5B shows the CT image of each of the four slices 80, 82, 84 and 86. As can be seen in the slices, slice 80 shows no sign of needle 74, slice 82 shows a sign of the needle and slices 84 and 86 show strong signs of the needle. It will be noted that the positions of the needles in the slices is different. From these different positions, it is possible to determine the three dimensional direction of insertion of the needle and the position of its tip.

Based on this information, which is preferably acquired continuously, both the position of the ROI can be easily determined and this information can be used additionally to or instead of the method described in conjunction with FIGS. 3 and 4, to center the reconstruction ROI in one or all of the slices. Furthermore, in accordance with an especially preferred embodiment of the invention the scanner may be programmed to "look" for signs of the entry of the needle in the next slice (slice 80 in this case) and move the patient such that for future scans the tip of the needle is imaged in one of the central slices.

Thus, in a preferred embodiment of the invention, during biopsy, both the position of the ROI and the position of the multiple slices with respect to the needle tip is automatically changed in response to the determination of the position of the tip of the needle. Alternatively or additionally, the entire image may be periodically recentered in response to the determination of the position of the needle, for example, when the entire image is periodically reconstructed.

While in a preferred embodiment of the invention, the scan is continuous, in other preferred embodiments of the invention, discreet scan are taken, for example, one per second. Alternatively or additionally, the radiation is stopped or the frequency of the scan is reduced if there is no movement for a predetermined time. In some embodiments of the invention, for example when the movement is relatively uniform, low pitch spiral scan, substantially equal to the velocity of the needle tip in the direction of the CT axis, may be performed. Preferably however, this movement is directly controlled, on a step by step basis, by the determination of movement as described above.

Alternatively to automatic movement of the patient to center the needle, in an alternative preferred embodiment of the invention, the physician performing the biopsy is first warned of the need for moving the patient and signifies his approval of the movement before it takes place, for example, by pressing a foot pedal. In this manner, movement of the patent during delicate movement of the biopsy needle is avoided.

It will be understood that the preferred embodiments described above are cited by way of example, and the full scope of the invention is limited only by the claims.

What is claimed is:

1. A method for modifying a planar image slice in a CT scanner having a predetermined reconstruction angle, comprising:

collecting X-ray attenuation data over a plurality of sectors, each sector having an angular extent substantially less than a reconstruction angle;

reconstructing an image of the slice using initial X-ray attenuation data acquired along an initial scan path sector including a contiguous subset of the plurality of sectors that span the reconstruction angle; and modifying the image in accordance with a difference between the radiation attenuation data collected in (1) one of the sectors of the subset of sectors and (2) one of the sectors outside of the subset of sectors, to provide a modified image of the slice.

2. A method according to claim 1, and comprising defining a region of interest within the image slice, wherein modifying the image comprises modifying only a portion of the image corresponding to the region of interest.

3. A method according to claim 2, wherein defining the region of interest comprises identifying an object of interest and altering the region of interest in response to movement of the object.

4. A method for modifying a planar image slice in a CT scanner having a predetermined reconstruction angle, the method comprising:
   reconstructing an image of the slice using initial X-ray attenuation data acquired along an initial scan path sector;
   acquiring additional X-ray attenuation data along an additional scan path sector in a vicinity of the axial position of the slice, the sector having an angular extent substantially less than the reconstruction angle;
   defining a region of interest within the image slice to include an object of interest;
   determining a characteristic of the X-ray attenuation data indicative of the position of the object;
   shifting the region of interest in response to a change in the characteristic; and
   modifying a portion of the image corresponding to the region of interest to provide a modified image of the slice, responsive to the additional attenuation data.

5. A method according to claim 4, wherein determining the characteristic of the X-ray attenuation data comprises finding a maximum value of the data within a data window corresponding to the region of interest.

6. A method according to claim 5, wherein finding the maximum value of the data comprises pre-processing the data and finding a maximum value of the pre-processed data.

7. A method according to claim 4, wherein the data along the initial and additional scan path sectors comprises acquiring multi-slice data acquired along the sectors of the scan path.

8. A method according to claim 4, wherein data acquired along the sectors of the scan path comprises data acquired along sectors of a helical scan path.

9. A method according to claim 7, wherein data acquired along the scan path sectors comprises data acquired along sectors of a generally circular scan path substantially within a plane at the axial position of the slice.

10. A method for modifying a planar image slice in a CT scanner having a predetermined reconstruction angle, the method comprising:
    reconstructing an image of the slice using initial X-ray attenuation data acquired along an initial scan path sector;
    acquiring additional X-ray attenuation data along an additional scan path sector in a vicinity of the axial position of the slice, the sector having an angular extent substantially less than the reconstruction angle;
    processing the additional attenuation data and the initial attenuation data to produce a difference image data matrix which represents a difference between corresponding initial attenuation data and additional attenuation data values; and
    adding the difference matrix to the image.

11. A method for modifying a planar image slice in a CT scanner having a predetermined reconstruction angle, comprising:
    reconstructing an image of the slice using initial X-ray attenuation data acquired along an initial scan path sector;
    acquiring additional X-ray attenuation data along an additional scan path sector in a vicinity of the axial position of the slice, the sector having an angular extent substantially less than the reconstruction angle;
    back-projecting attenuation values calculated from the additional data, to determine a first preliminary matrix;
    back-projecting attenuation values calculated from the initial data that were acquired in a portion of the initial scan path sector corresponding to the additional scan path sector, to determine a second preliminary matrix;
    subtracting the second preliminary matrix from the first preliminary matrix to produce an image data matrix; and
    adding the produced image data matrix to the image.

12. A method for modifying a planar image slice in a CT scanner having a predetermined reconstruction angle, comprising:
    reconstructing an image of the slice using initial X-ray attenuation data acquired along an initial scan path sector;
    acquiring additional X-ray attenuation data along an additional scan path sector in a vicinity of the axial position of the slice, the sector having an angular extent substantially less than the reconstruction angle;
    calculating initial attenuation values from the initial data that were acquired in a portion of the initial scan path sector corresponding to the additional scan path sector;
    calculating additional attenuation values from the additional data;
    subtracting the initial attenuation values from the additional attenuation values to determine difference values;
    back-projecting the difference data to produce an image data matrix; and
    adding the produced image data matrix to the image.

13. A method according to claim 4, and comprising superimposing the CT image of the region of interest on another CT image encompassing a substantially greater portion of the cross-sectional area.

14. A method according to claim 13 wherein the updated image of the region of interest is produced utilizing the following method:
    reconstructing an image of the slice using initial X-ray attenuation data acquired along an initial scan path sector; and
    modifying the image to provide a modified image of the slice, responsive to additional X-ray attenuation data acquired along an additional scan path sector in a vicinity of the axial position of the slice, the sector having an angular extent substantially less than a predetermined reconstruction angle.

15. A method for producing a CT image of a region of interest within a body of a subject, the method comprising:
    reconstructing a CT image of a slice of the body;
    defining a region of interest within the CT image which includes an object of an interest;
    altering the region of interest being reconstructed in response to a movement of the object, wherein altering the region of interest in response to movement of the object comprises determining a characteristic of the X-ray attenuation data indicative of the position of the object, and shifting the region of interest being reconstructed in response to a change in the characteristic; and updating the CT image only in the region of interest.

16. A method according to claim 15 wherein the region of interest is determined based on an expectation of a change in the CT image in the region of image.

17. A method according to claim 15, and including identifying an object of interest and wherein defining the region of interest comprises defining the region of interest in response to a determination of the position of the object of interest.

18. A method according to claim 15, wherein determining the characteristic of the X-ray attenuation data comprises finding an extremum value of the data within a data window corresponding to the region of interest.

19. A method according to claim 18, wherein finding the extremum value of the data comprises preprocessing the data and finding a maximum value of the pre-processed data.

20. A method according to claim 15 wherein the CT image is a multi-slice image and wherein the position of the slices are determined based on a determination of the position of the object with respect to the slices.

21. A method of determining an optimal position for multiple CT slices, the method comprising:
    reconstructing multiple slices based on a first set of data;
    displaying one of the slices in accordance with the determined position;
    determining a region of interest in the displayed slice adjacent the object; and
    during movement of the object, monitoring the position of the moving object and automatically at least one of (i) moving and updating the region of interest in the displayed slice and (ii) displaying and updating another of the reconstructed slices to track the movement of the object.

22. A method according to claim 15 wherein the object is a biopsy needle.

23. An imaging method for imaging a region in a region of interest in which changes are expected comprising:
    reconstructing an image using initial X-ray attenuation data acquired along an initial scan path including a plurality of sectors;
    defining a region of interest in the reconstructed image;
    monitoring additional X-ray attenuation data through the region of interest acquired along an additional scan path sector having an angular extent substantially less than a predetermined reconstruction angle;
    periodically modifying the reconstructed image in response to changes in the monitored X-ray attenuation data.

24. An imaging method including:
    collecting X-ray attenuation data along a scan path;
    reconstructing an initial volume CT image of the body, the volume image including a plurality of slices, each slice reconstructed using a portion of the initial X-ray attenuation data acquired along an initial scan path sector spanning a predetermined reconstruction angle;
    defining a region of interest which encompasses only a portion of the CT image;
    periodically modifying a displayed one of the slices including:
    modifying the displayed slice to provide the updated display of a slice, responsive to additional X-ray attenuation data acquired along an additional scan path sector in a vicinity of the axial position of the slice, the sector having an angular extent substantially less than the predetermined reconstruction angle.

25. An imaging method for a determination of a position of a biopsy needle including:
    reconstructing a CT image from a plurality of views;
    determining the position of the biopsy needle in the image;
    determining a region of interest based on the determined position of the biopsy needle; and
    periodically modifying the image only in the region of interest, including:
    reconstructing an initial image using initial X-ray attenuation data acquired over a predetermined reconstruction angle along an initial scan path sector; and
    modifying the initial image to provide an updated image, responsive to additional X-ray attenuation data acquired along an additional scan path sector in a vicinity of the axial position of the slice, the sector having an angular extent substantially less than the predetermined reconstruction angle.

26. The method according to claim 23 wherein the periodically modifying of the image uses the following method:
    reconstructing an initial image of the slice using initial X-ray attenuation data acquired along an initial scan path sector; and
    modifying the image to provide a modified image of the slice, responsive to additional X-ray attenuation data acquired along an additional scan path sector in a vicinity of the axial position of the slice, the sector having an angular extent substantially less than a predetermined reconstruction angle.

* * * * *